(12) United States Patent
Seung et al.

(10) Patent No.: US 6,866,963 B2
(45) Date of Patent: Mar. 15, 2005

(54) CATHODE ACTIVE MATERIAL AND LITHIUM BATTERY EMPLOYING THE SAME

(75) Inventors: Do-Young Seung, Yongin (KR); Won-cheol Jung, Daejeon (KR); Chil-hoon Do, Changwon (KR); Sung-in Moon, Changwon (KR)

(73) Assignee: Samsung SDI Co., Ltd., Kyungki-do (KR)

( * ) Notice: Subject to any disclaimer, the term of this patent is extended or adjusted under 35 U.S.C. 154(b) by 344 days.

(21) Appl. No.: 09/888,435

(22) Filed: Jun. 26, 2001

(65) Prior Publication Data

US 2002/0055039 A1 May 9, 2002

(30) Foreign Application Priority Data

Sep. 4, 2000 (KR) .................................... 2000-52208
Jun. 12, 2001 (KR) .................................... 2001-32952

(51) Int. Cl.[7] .............................................. H01M 4/60
(52) U.S. Cl. ........................ 429/212; 68/18; 68/21; 68/23; 68/25; 429/213
(58) Field of Search ............................. 429/212, 213; 568/18, 21, 23, 25

(56) References Cited

U.S. PATENT DOCUMENTS 3,621,032 A * 11/1971 Aryan et al. .................. 549/11

OTHER PUBLICATIONS

Seung et al, "Development of Environmentally Acceptable High–energy Lithium/Sulfur Polymer Electrolyte Battery (LSPB)", Seminar on Advanced Environmental Technology Developments, Korea, (Jun. 26, 2000).

Seung et al, "Development of Lithium Secondary Battery using Organopolysulfide Compound", Seminar on Advanced Environmental Technology Development Projects, (Jun. 11, 2001).

"An Aromatic Bis–tetrasulfide as Cathode Active Material for Sulfur Battery", Seminar on Advanced Environmental Technology Development Projects, (Jun. 11, 2001).

* cited by examiner

Primary Examiner—Bruce F. Bell
Assistant Examiner—Monique Wills
(74) Attorney, Agent, or Firm—Lee & Sterba, P.C.

(57) ABSTRACT

A cathode active material and a lithium secondary battery employing the same are provided. In the cathode active material includes cyclic bis (2,5-bis-dithio-1,4-dimethoxybenzene) represented by formula 1:

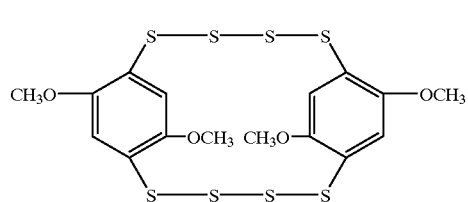

5 Claims, 10 Drawing Sheets

CATHODE ACTIVE MATERIAL AND LITHIUM BATTERY EMPLOYING THE SAME

BACKGROUND OF THE INVENTION

1. Field of the Invention

The present invention relates to a cathode active material and a battery employing the same, and more particularly, to an organopolysulfide cathode active material, the particle size of which is easy to process, and which has excellent electrochemical utilization efficiency and capacity, and to a lithium battery employing the same.

2. Description of the Related Art

As the use of portable devices has rapidly increased, there has been a gradually increasing necessity for high-performance secondary batteries. Also, the miniaturization of such portable devices has fueled the desire for development of light-weight, high-energy density secondary batteries.

In conventional secondary batteries, although light-weight and high-capacity performance has been achieved to an extent, environmental problems due to the use of heavy metal arise. Thus, secondary batteries using environmentally benign materials have become keenly required.

In attaining high-capacity batteries, one of the critical issues is to develop low equivalent weight electrode active materials. Here, the electrode active materials must have sufficient ionic conductivity and high reversibility of an oxidation/reduction reaction, as well as excellent thermal and chemical stability. Also, the electrode materials must be reasonably inexpensive, widely available, non-toxic, and easy to process.

As cathode active materials having the above-described required characteristics, the following organo-sulfur compounds are known.

Polyplus Battery Company, Inc. has developed an organosulfur cathode active material represented by general formula $(R(S)_y)_n$, wherein R is an organic group having 1 to 20 carbon atoms, y is an integer from 1 to 6 and n is an integer from 2 to 20. The battery utilizing this cathode material has a poor lifetime characteristic, although it exhibits excellent energy density.

Organosulfur cathode active materials disclosed in U.S. Pat. Nos. 5,686,201 and 5,532,077, although having an excellent energy density, have a poor cycle characteristic and a low electric capacity of approximately 67%, that is, a necessity of charging 150% of a discharge electric capacity.

Known cathode active materials developed by Moltech Corporation include $(CS_x)_n$, wherein x is 1.7–2.3 and n is an integer from 2 to 20, and $(C_2S_x)_n$ wherein x is 1–10 and n is greater than or equal to 2 (U.S. Pat. No. 5,529,860). Those cathode active materials have theoretically high specific capacity but have poor utilization efficiency, low reversibility of the oxidation/reduction reaction, that is, charging/discharging reaction, and relatively low electric capacity due to a restricted amount of sulfur participating in the electrochemical reaction, resulting from the formation of an insulating sulfur film on an electrode portion.

SUMMARY OF THE INVENTION

It is a first feature of the present invention to provide a cathode active material which has not only excellent electrochemical utilization efficiency and capacity characteristics but also high reversibility of the charging/discharging reaction. and which also has a particle size which is easy to process.

It is a second feature of the present invention to provide a highly efficient lithium battery having excellent capacity and cycle characteristics by employing the cathode active material.

It is a third feature of the present invention to provide new organopolysulfide compounds usable as a cathode active materials.

It is a fourth feature of the present invention to provide a cathode active material containing the novel organopolysulfide compounds.

It is a fifth feature of the present invention to provide a lithium battery employing the cathode active material.

In accordance with one aspect of the present invention, there is provided a cathode active material including cyclic bis (2,5-bis-dithio-1,4-dimethoxybenzene) represented by formula 1:

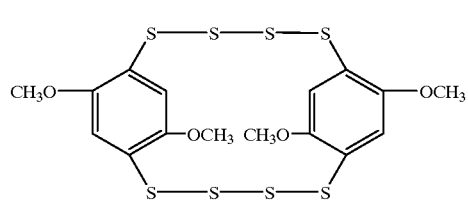

In accordance with another aspect of the present invention, there is provided a lithium secondary battery including a cathode having a cathode active material layer comprising cyclic bis (2,5-bis-dithio-1,4-dimethoxybenzene) represented by formula 1, a conductive agent and a binder; an anode having an anode layer comprising lithium metal or a lithium alloy; and a separator interposed between the cathode and the anode:

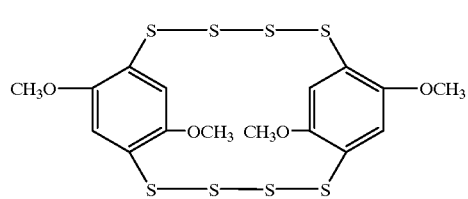

In accordance with a further aspect of the present invention, there is provided an organopolysulfide represented by formulas 2 or 3:

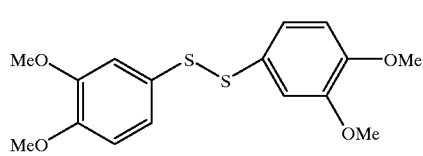

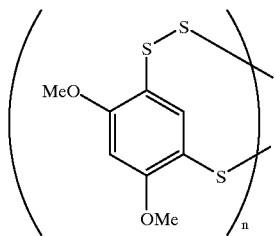

3 wherein n is an integer from 2 to 10.

According to an additional aspect of the present invention, there is provided an organopolysulfide which is a reaction product of sulfur monochloride and a compound represented by formula 4:

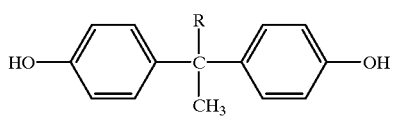

4 wherein R is a hydrogen atom or a methyl group.

The synthesis formula of the reaction product of sulfur monochloride and a compound represented by formula 4 in which R is a hydrogen atom, is $(C_{14}H_{10}O_2S_8)_n$, and can be represented by formula 5, and the synthesis formula of the reaction product of sulfur monochloride and a compound represented by formula 4 in which R is a methyl group, is $(C_{14}H_{10}O_2S_8)_n$, and can be represented by formula 6:

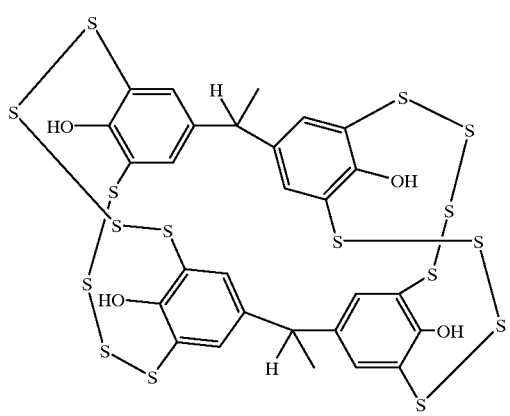

5

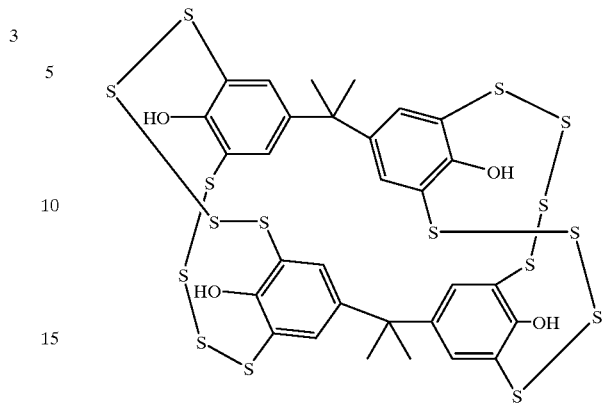

6

According to still another aspect of the present invention, there is provided an organopolysulfide represented by formula 7:

7 wherein R is a hydrogen atom or a methyl group.

The synthesis formula of the organopolysulfide is $C_6S_{18}$, which is a reaction product of sulfur and hexabromobenzene in the presence of ammonia.

In accordance with yet another aspect of the present invention, there is provided a cathode active material containing an organopolysulfide represented by one of formulas 2 through 7.

In accordance with another aspect of the present invention, there is provided a lithium battery employing a cathode active material as described above.

In more specific embodiments, the synthesis formula of the organosulfide represented by formula 2 is $C_{16}H_{18}O_{.4}S_2$, and the synthesis formula of the organopolysulfide represented by formula 3 is $(C_8H_8O_2S_3)_n$, wherein n is an integer of 2 through 10.

BRIEF DESCRIPTION OF THE DRAWINGS

The above features and advantages of the present invention will become more apparent by describing in detail a preferred embodiment thereof with reference to the attached drawings in which.

DESCRIPTION OF THE PREFERRED EMBODIMENTS

Figure 1:
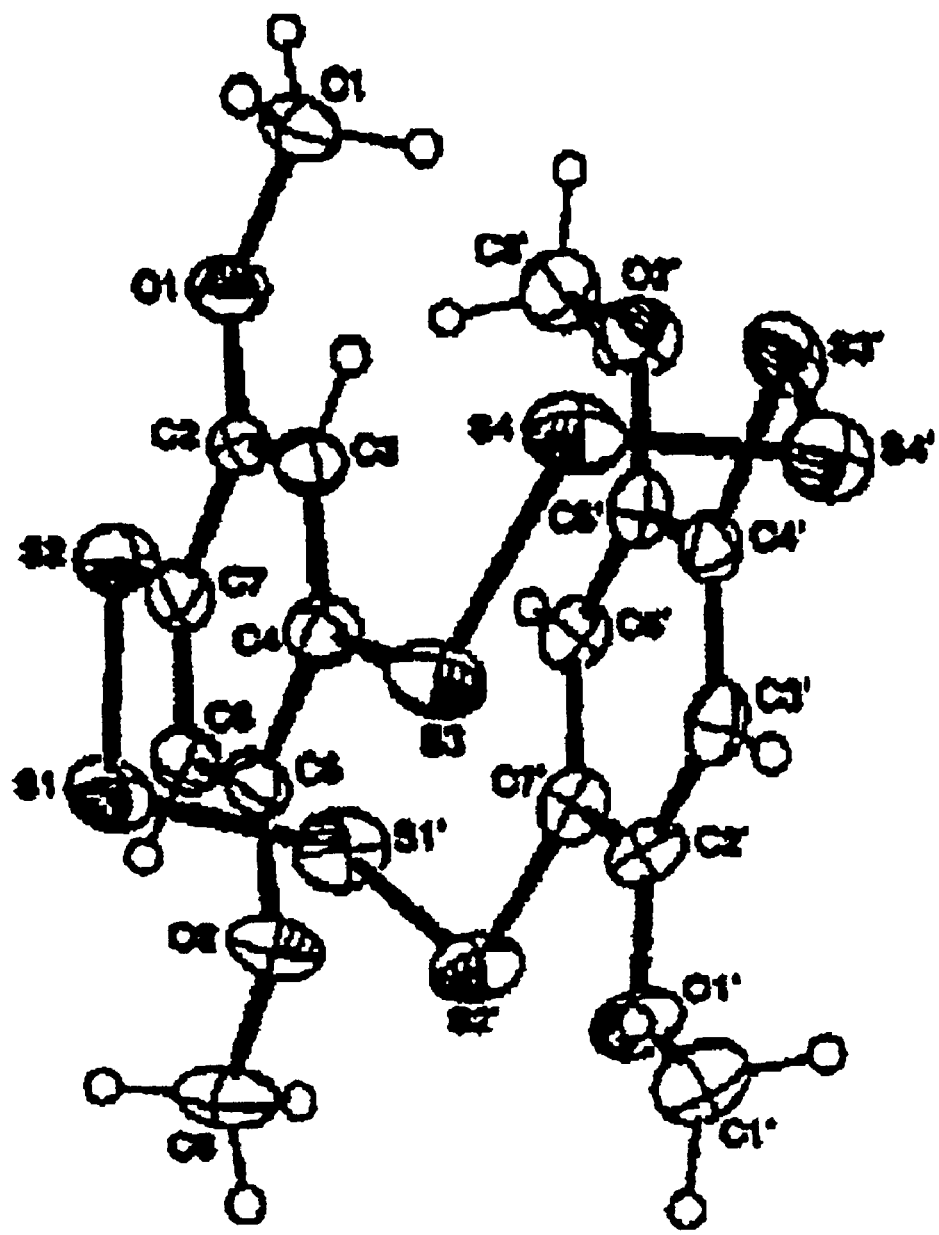
FIG. 1 illustrates the X-ray crystal structure of the organopolysulfide prepared by Synthesis Examples 5 and 6 of the present invention.

Priority Korean Patent Applications No. 00-52208, filed Sep. 4, 2000, and No. 01-32952, filed Jun. 12, 2001, are hereby incorporated in their entireties by reference.

The present invention is directed to environmentally benign batteries in which heavy metallic materials such as nickel, cobalt, manganese and the like, which have been used as cathode active materials of conventional secondary batteries, are replaced by non-metallic sulfur compounds.

Sulfur compounds are generally used as high-capacity active materials but the particle sizes thereof are not easy to process. This results in deterioration of the electrochemical utilization efficiency.

However, cyclic bis (2,5-bis-dithio-1,4-dimethoxybenzene) represented by formula 1 according to the present invention is easy to process with respect to particle size and has excellent electrochemical utilization efficiency and specific capacity. This compound is known from U.S. Pat. No. 3,719,645 and, conventionally, has been used mainly in binders, specifically in metal-to-metal binders.

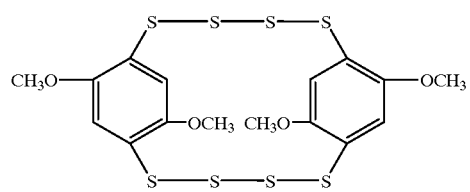

1

In conventional secondary batteries using $LiCoO_2$, $LiNiO_2$, $LiMn_2O_4$ or composite metal oxides thereof as a cathode active material, the battery voltage ranges from 3.5 to 3.7 V.

On the other hand, when cyclic bis (2,5-bis-dithio-1,4-dimethoxybenzene) represented by formula 1 according to the present invention is used as a cathode active material, the battery voltage is approximately 2 V with respect to lithium, which is in a stable range of a potential window for conventional solid polymer electrolytes.

In the lithium secondary battery according to the present invention, a solid polymer electrolyte functions as a conductive medium for lithium ions and as a separator.

Cyclic bis (2,5-bis-dithio-1,4-dimethoxybenzene) represented by formula 1 has a synthesis formula of $C_{16}H_{16}O_4S_8$ and a molecular weight of 528 g/mol, and has a backbone forming an electron conductivity passage by p-orbital conjugation, thereby facilitating donation and acceptance of electrons in the electrochemical reaction of low conductivity sulfur. In other words, cyclic bis (2,5-bis-dithio-1,4-dimethoxybenzene) represented by formula 1 is a cathode active material which can encourage the high-capacity characteristic of sulfur, provide conductivity by being bonded with a conductive polymer and suppress the structural change caused by the polymerization/depolymerization of sulfur.

Furthermore, cyclic bis (2,5-bis-dithio-1,4-dimethoxybenzene) represented by formula 1, having a theoretically high capacity of 610 mAh/g, has excellent stability against air, humidity and heat, is insoluble in an electrolytic solution and highly competitive in price, and is easily separated and refined.

A battery employing cyclic bis (2,5-bis-dithio-1,4-dimethoxybenzene) represented by formula 1 as a cathode active material, will now be described.

First, a conductive agent, a binder, a lithium salt and a solvent are added to a cathode active material, that is, cyclic bis (2,5-bis-dithio-1,4-dimethoxybenzene) represented by formula 1, and then sufficiently mixed to prepare a cathode active material composition. Then, the cathode active material composition is coated on a cathode current collector and dried to form a cathode active material layer, thereby fabricating a cathode.

In particular embodiments of the cathode active material composition, carbon black, acetylene black or vapor growth carbon fiber (VGCF) is used as the conductive agent. The content of the conductive agent is about 5 to about 20 parts by weight based on 100 parts by weight of solid matter of the cathode active material composition, more preferably about 13 to about 17 parts by weight, most preferably about 15 parts by weight. Here, if the content of the conductive agent is greater than about 20 parts by weight, it is difficult to cast the active material composition on the cathode current collector. If the content of the conductive agent is less than about 5 parts by weight, the resistance of the cathode is quite high, resulting in difficulty in performing charging/discharging.

As the binder, the same material as the polymer resin for forming the polymer matrix used as a separator is preferably used. Non-limiting examples of the binder include polyethylene oxide (PEO), polyacrylonitrile (PAN), polymethyl methacrylate (PMMA), polyvinylidene fluoride (PVDF), acrylonitrile-methylmethacrylate-styrene terpolymer (AMS), vinylidene fluoride-hexafluoropropylene (VDF-HFP) copolymer, polyvinyl chloride (PVC) and cellulose. The content of the binder is about 10 to about 35 parts by weight based on 100 parts by weight of solid matter of the cathode active material, more preferably about 20 to about 32 parts by weight. Here, if the content of the binder is greater than about 35 parts by weight, the content of the cathode active material is relatively reduced. If the content of the binder is less than about 10 parts by weight, the content of the conductive medium for lithium ions is relatively reduced, resulting in a reduction of lithium ionic conductivity. As a result, the resistance of a cathode is undesirably high, which makes it difficult to perform charging/discharging.

The content of the compound represented by formula 1, which is a cathode active material, is preferably about 55 to about 90 parts by weight based on 100 parts by weight of the solid matter of the cathode active material composition, more preferably about 55 to about 70 parts by weight, and most preferably approximately 65 parts by weight. Here, if the content of the cathode active material is greater than about 90 parts by weight, the contents of the conductive agent, the binder and the lithium salt are relatively reduced, making it more difficult to conduct electrons and lithium ions. This results in an increase in the electrode resistance and difficulty in charging/discharging. If the content of the cathode active material is less than about 10 parts by weight, that is, the content of the same contained in an electrode is relatively small, the specific capacity of the electrode is undesirably reduced.

The lithium salt is not specifically restricted and any lithium compound that is dissociated from an organic solvent to produce lithium ions can be used. Non-limiting examples thereof include at least one ionic lithium salt selected from the group consisting of lithium perchlorate ($LiClO_4$), lithium tetrafluoroborate ($LiBF_4$), lithium hexafluorophosphate ($LiPF_6$), lithium trifluoromethansulfonate ($LiCF_3SO_3$) and lithium bis(trifluoromethansulfonyl) amide ($LiN(CF_3SO_2)_2$). The content of the lithium salt is preferably about 2 to about 4 parts by weight based on 100 parts by weight of the solid matter of the cathode active material composition. If the content of the lithium salt is greater than about 4 parts by weight, the ionization efficiency of lithium ions is reduced and the lithium salt is precipitated when fabricating a cathode. If the content of the lithium salt is less than about 2 parts by weight, the content of lithium ions contained in the cathode is undesirably reduced.

Any material that can dissolve the binder and the lithium salt and can disperse the cathode active material and the conductive agent, and is easily volatile, can be used as the solvent. Usable solvents include, without limitation, acetonitrile, N-methylpyrrolidone, dimethylformamide, hexane, acetone and the like, and the content thereof is preferably about 250 to about 730 parts by weight based on 100 parts by weight of the solid matter of the cathode active material composition. Here, if the content of the solvent is greater than about 730 parts by weight, the viscosity of the cathode active material composition decreases, which makes it difficult to cast the cathode active material. If the content of the solvent is less than about 250 parts by weight, the non-homogeneity of the cathode active material composition becomes serious and casting of the composition is difficult due to high viscosity.

Separately from the above, lithium metal or a lithium alloy, which is an anode active material, is preferably roll-pressed on an anode current collector to form an anode active material layer, thereby producing an anode. Here, like in the cathode, additives such as a conductive agent or a binder can be added to the lithium metal or the lithium alloy, as necessary.

A separator is interposed between the cathode and the anode and then the resultant structure is sequentially stacked to then be sealed under vacuum. Then, the sealed battery is aged, thereby completing a lithium secondary battery.

The lithium battery according to the present invention is not specifically restricted, but is preferably a lithium/sulfur polymer electrolyte battery using a solid polymer electrolyte as a separator.

An electrolyte prepared, for example, by impregnating an electrolytic solution into commercially available porous polypropylene (product name: Celgard 2500), porous polyethylene or porous polyethylene-polypropylene multiple layer, is preferably used as the solid polymer electrolyte. Here, the electrolytic solution is composed of a lithium salt and an organic solvent. The same lithium salt as in the composition for forming the cathode active material is preferably used. Also, at least one solvent selected from the group consisting of propylene carbonate (PC), ethylene carbonate (EC), y-butyrolactone, 1,3-dioxolane, dimethoxyethane, dimethyl carbonate (DMC), diethyl carbonate (DEC), methyl ethyl carbonate (MEC), tetrahydrofuran (THF), dimethylsulfoxide and polyethyleneglycol dimethyl ether, is preferably used as the organic solvent. The contents of the lithium salt and the solvent are preferably the same as those in the conventional lithium secondary battery.

The solid polymer electrolyte of the present invention can also be used in the following manner rather than in the above-described manner.

First, a polymer resin, a filler, a solvent and a lithium salt are mixed to prepare a solid polymer electrolyte composition. The composition is directly coated on the anode and dried to obtain the solid polymer electrolyte. Otherwise, the solid polymer electrolyte composition can be obtained such that the composition for forming the solid polymer electrolyte is cast on a separate support body and dried, and then a solid polymer electrolyte film exfoliated from the support body is laminated on the anode. Here, any material that functions to support the solid polymer electrolyte film can be used as the support body, and usable materials include, without limitation, a glass substrate, a polyethylene terephthalate (PET) film, a mylar film and the like.

The polymer resin is not specifically restricted, but any material that can be used as a binder of a cathode, can be used as the polymer resin. Usable polymer resins include, without limitation, polyethylene oxide (PEO), polyacrylonitrile (PAN), polymethyl methacrylate (PMMA), polyvinylidene fluoride (PVDF), acrylonitrile-methyl methacrylate-styrene terpolymer (AMS), vinylidene fluoride-hexafluorpropylene (VDF-HFP) copolymer, polyvinyl chloride (PVC), cellulose or the like.

The filler serves to improve the mechanical strength of the solid polymer electrolyte, and non-limiting examples of usable fillers include silica, caoline, alumina, zeolite and the like. The content of the filler is preferably about 2 to about 10 parts by weight based on 100 parts by weight of the solid matter of the composition for forming the solid polymer electrolyte, more preferably about 5 parts by weight. Here, if the content of the filler is less than about 2 parts by weight, the ionic conductivity and mechanical property of the solid polymer electrolyte become weak. If the content of the filler is greater than about 10 parts by weight, the film formability undesirably deteriorates.

Also, in the composition for forming a solid polymer electrolyte, the solvent is a material which is capable of dissolving or dispersing a polymer resin, a filler and a lithium salt. Usable solvents include, without limitation, acetonitrile, N-methylpyrrolidone, dimethylformamide, hexane, acetone and the like. The content of the solvent is preferably about 1000 to about 1500 parts by weight based on 100 parts by weight of the solid matter of a composition for forming a solid polymer electrolyte. If the content of the solvent is less than about 1000 parts by weight, problems may be encountered with dispersion and casting of the composition and uniformity of layer thickness. If the content of the solvent is greater than about 1500 parts by weight, casting of the composition and adjustment of layer thickness are difficult to achieve.

In the composition for forming a solid polymer electrolyte, preferably the same lithium salt is used as that added to the cathode. The content of the lithium salt is preferably about 5 to about 15 parts by weight based on 100 parts by weight of the solid matter of the composition for forming the solid polymer electrolyte. Here, if the content of the lithium salt is less than about 5 parts by weight, the ionic conductivity of the solid polymer electrolyte become weak. If the content of the lithium salt is greater than about 15 parts by weight, dissociation of the lithium salt is made difficult and the film formability undesirably deteriorates.

In a lithium/sulfur polymer electrolyte battery according to the present invention, during discharging, the organopolysulfide which is a cathode active material, that is, cyclic bis (2,5-bis-dithio-1,4-dimethoxybenzene) represented by formula 1, reacts with metal M which is an anode material to produce a metal-sulfur compound in the organopolysulfide as represented by the following formula:

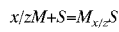

In other words, during discharging, the cathode is formed of a compound consisting of the organopolysulfide, metal and sulfur, and the discharging and charging reaction is reversible.

Also, the present invention provides organopolysulfides represented by the following formulas 2 or 3:

wherein the synthesis formula of the organopolysulfide represented by formula 2 is $C_{16}H_{18}O_4S_2$, and the synthesis formula of the organopolysulfide represented by formula 3 is $(C_8H_8O_2S_3)_n$, wherein n is an integer from 2 to 10.

The method of preparing the organopolysulfide represented by formulas 2 and 3 will now be described.

The organopolysulfide represented by formula 2 is prepared such that an organic solvent is added to 1,2-dimethoxybenzene, sulfur monochloride ($S_2Cl_2$) is further added thereto to be reacted, and then a work-up process is carried out.

Here, during the reaction between 1,2-dimethoxybenzene and sulfur monochloride, AO gases such as chlorine ($Cl_2$) or hydrogen chloride (HCl) are produced. Thus, while one end entrance of a container having the reactant mixture is closed, a gas trap device is connected to the other end entrance.

The organopolysulfide represented by formula 3 is prepared in the same manner as the organopolysulfide represented by formula 2, except that 1,3-dimethoxybenzene is used instead of 1,2-dimethoxybenzene.

Also, the present invention provides an organopolysulfide which is a reaction product of sulfur monochloride and a compound represented by formula 4:

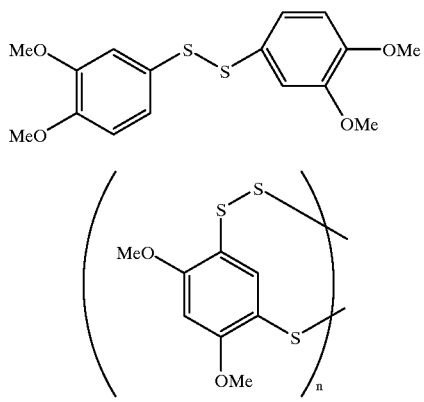

wherein R is a hydrogen atom or a methyl group.

In the formula 4, in the case where R is a hydrogen atom, the synthesis formula of the reaction product of sulfur monochloride and the compound represented by formula 4 is $(Cl_{14}H_{10}O_2S_8)_n$, and can be represented by formula 5:

wherein n is 1 or 2.

In the case where R is a methyl group, the synthesis formula of the reaction product of sulfurmonochloride and a compound represented by formula 4, is $(C_{14}H_{10}O_2S_8)_n$, and can be represented by formula 6:

wherein n is 1 or 2.

Also, the present invention provides an organopolysulfide represented by formula 7 and prepared by reacting sulfur and hexabromobenzene in the presence of ammonia:

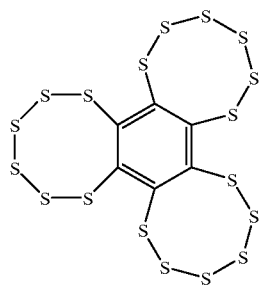

wherein the synthesis formula of organopolysulfide is $C_6S_{18}$.

The organopolysulfides represented by formulas 2, 3 or 5–7 can be used as a cathode active material like cyclic bis (2,5-bis-dithio-1,4-dimethoxybenzene) represented by formula 1, and can also be advantageously used as a vulcanizing (sulfur-containing) material.

Now, the present invention will be described in detail with reference to examples and synthesis examples, and the invention is not limited thereto.

SYNTHESIS EXAMPLE 1

Preparation of Organopolysulfide Represented by Formula 2

5 mmol of 1,2-dimethoxybenzene (to be abbreviated as DMB) (691 mg) was put into a 100 ml two-neck round-bottomed flask having a magnetic bar in a hood where ventilation efficiency is good, under a nitrogen atmosphere and then 10 ml of methylene chloride was added thereto. Next, 10 mmol of sulfur monochloride ($S_2Cl_2$) (to be abbreviated to as SMC) (1.0 M, 2 equivalents) was injected at room temperature over a 1 minute period using a syringe having a gas preventing structure, and then the reaction mixture was stirred. One end entrance of the flask was closed with a rubber cap, and the other end entrance was opened so that gases such as chloride or hydrogen chloride could escape, and a NaOH trap device was added thereto.

The reaction mixture so obtained was stirred for 2 hours, and then allowed to stand, without stirring. After a lapse of one day, black needle-shaped crystals were produced from the reaction mixture. After a lapse of 10 days, the crystals so produced were filtered. Subsequently, the reaction mixture was washed using 2 ml of methylene chloride and dried under vacuum, thereby obtaining 340 mg of an organopolysulfide represented by formula 2.

SYNTHESIS EXAMPLE 2

Preparation of Organopolysulfide Represented by Formula 2

342 mg of an organopolysulfide represented by formula 2, which is a black needle-shaped solid, was obtained in the same manner as in Synthesis Example 1, except that 4 equivalents, rather than 2 equivalents, of SMC were used.

Elemental analysis was carried out for the organopolysulfides represented by formula 2 obtained by Synthesis Examples 1 and 2 using an elemental analyzer, to measure the content of sulfur related to the battery capacity.

The measurement result showed that the ratio of carbon (C) to hydrogen (H) to sulfur (S) was 56.8:5.3:18.9, in the organopolysulfide represented by formula 2 prepared by Synthesis Examples 1 and 2.

SYNTHESIS EXAMPLE 3

Preparation of Organopolysulfide (n=2–10) Represented by Formula 3

5 mmol of 1,3-DMB (691 mg) was put into a 100 ml two-neck round-bottomed flask having a magnetic bar, placed in a hood where ventilation efficiency is good, Pro under a nitrogen atmosphere, and then 100 ml of methylene chloride was added thereto. Next, 10 mmol of SMC (1.0 M, 2 equivalents) was injected at room temperature over a 1 minute period using a syringe having a gas preventing structure, and then the reaction mixture was stirred. One end entrance of the flask was closed with a rubber cap, and the other end entrance was opened so that gases such as chlorine or hydrogen chloride could escape, and a NaOH trap device was added thereto.

In the course of stirring the reaction mixture, large amounts of gases were produced and the color of the reaction mixture was red.

The reaction mixture so obtained was stirred for 5 minutes, and then allowed to stand, without stirring. After a lapse of one day, the color of the reaction mixture turned to orange-red. After a lapse of 10 days, there was no further change in the color of the reaction mixture. Subsequently, the reaction mixture was vacuum-distilled at 100° C. to remove unreacted SMC and methylene chloride and then dried, thereby obtaining 1.04 g of an organopolysulfide represented by formula 3, which is a red, sticky solid.

SYNTHESIS EXAMPLE 4

Preparation of Organopolysulfide Represented by Formula 3

1.08 g of an organopolysulfide represented by formula 3, which is a red sticky solid, was obtained in the same manner as in Synthesis Example 3, except that 4 equivalents, rather than 2 equivalents, of SMC were used.

Elemental analysis was carried out for the organopolysulfides represented by formula 3 obtained by Synthesis Examples 3 and 4 using an elemental analyzer, to measure the content of sulfur related to the battery capacity.

The measurement result showed that the ratio of carbon (C) to hydrogen (H) to sulfur (S) was 41.4:3.4:41.7, in the organopolysulfide represented by formula 3 prepared by Synthesis Examples 3 and 4.

SYNTHESIS EXAMPLE 5

Preparation of cyclic bis (2,5-bis-dithio-1,4-dimethoxybenzene) Represented by Formula 1

20 mmol of 1,4-DMB (2.76 mg) was put into a 100 ml two-neck round-bottomed flask having a magnetic bar, placed in a hood where ventilation efficiency is good, under a nitrogen atmosphere and then 20 ml of methylene chloride was added thereto. Next, 10 mmol of SMC (1.0 M, 2 equivalents) was injected at room temperature over a 1 minute period using a syringe having a gas preventing structure, and then the reaction mixture was stirred. Here, one end entrance of the flask was closed with a rubber cap, and the other end entrance was opened so that gases such as chlorine or hydrogen chloride could escape, and a NaOH trap device was added thereto.

The reaction mixture so obtained was stirred for 30 minutes, and then allowed to stand. The color of the reaction mixture gradually turned to light green. After a lapse of three days, red-orange crystals were produced from the reaction mixture, and were then allowed to stand for one week, thereby further producing crystals. The solid so produced was filtered and then washed using 10 ml of methylene chloride and dried under a vacuum condition, thereby obtaining 1.96 g of a red-orange organopolysulfide, that is, cyclic bis (2,5-bis-dithio-1,4-dimethoxybenzene) represented by formula 1. Here, it was confirmed that the filtrate contained 1.37 g of 2,5-dichloro-1,4-DMB due to chlorination of 1,4-DMB, after filtering the solid organopolysulfide.

The melting point of the organopolysulfide was 197–200° C., and the result of the analysis of the molecular structure of the solid crystal based on the X-ray crystallization method is shown in FIG. 1. The molecular weight, density and theoretical specific capacity of the crystal were 528 g/mol, 1.56 g/cm$^3$ and 610 mAh/g, respectively.

Figure 3:
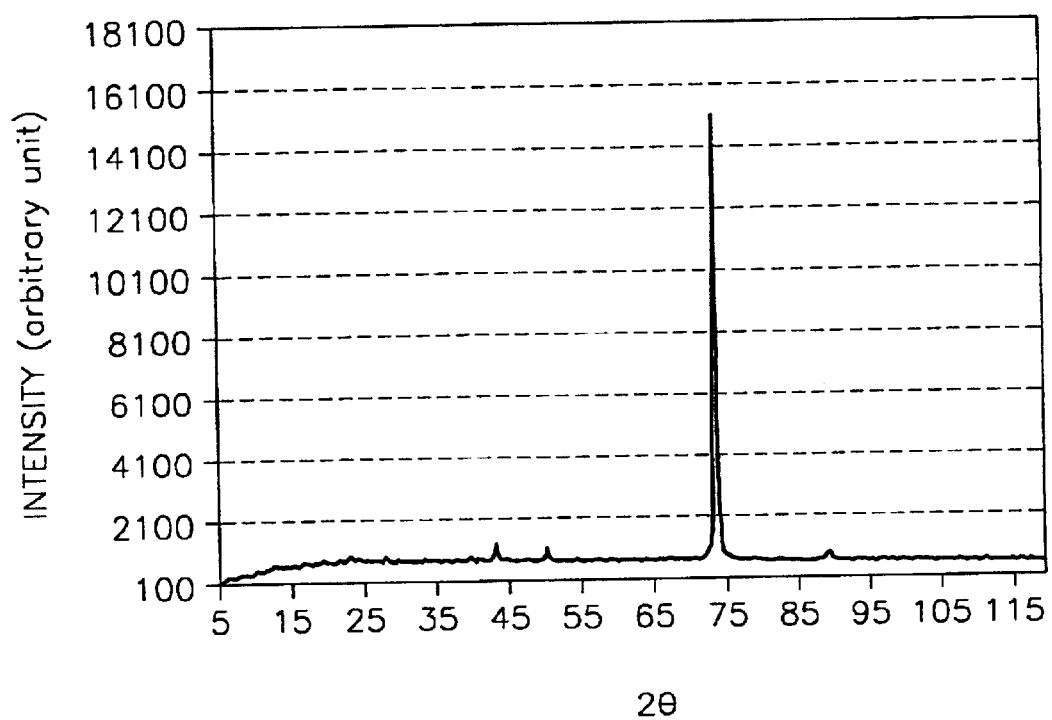
FIG. 3 is a graphic representation illustrating the result of an analysis of the crystallinity of the organopolysulfide prepared by Synthesis Examples 5 and 6 of the present invention.

FIG. 3 is a graph showing the crystallinity of the organopolysulfide prepared by Examples 5 and 6. Referring thereto, the prepared materials turned out to be of the same kind. In FIG. 3, a peak at which 2θ is 75 is produced due to a current collector. Thus, it was confirmed that the crystallinity of an electrode using the organopolysulfide as a cathode active material was very low, that is, the amorphousness thereof was high.

The particle size characteristics of the organopolysulfide were analyzed as follows.

First, the organopolysulfide was dispersed in ethanol and then pulverized using an RM100 mortar grinder. Subsequently, the solvent was removed from the resultant material and vacuum-dried. The resultant material was pulverized and then the distribution characteristics of particle sizes before and after pulverization were compared.

Figure 2A:
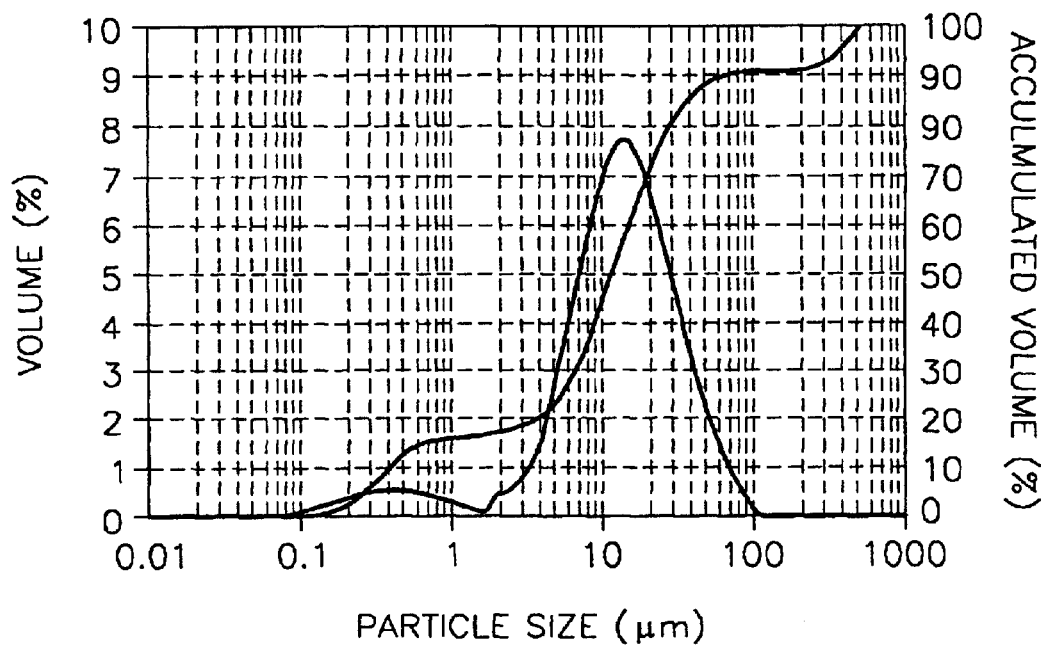
FIGS. 2A and 2B are graphic representations illustrating the distribution of particle sizes of the organopolysulfide prepared by Synthesis Examples 5 and 6 of the present invention.
Figure 2B:
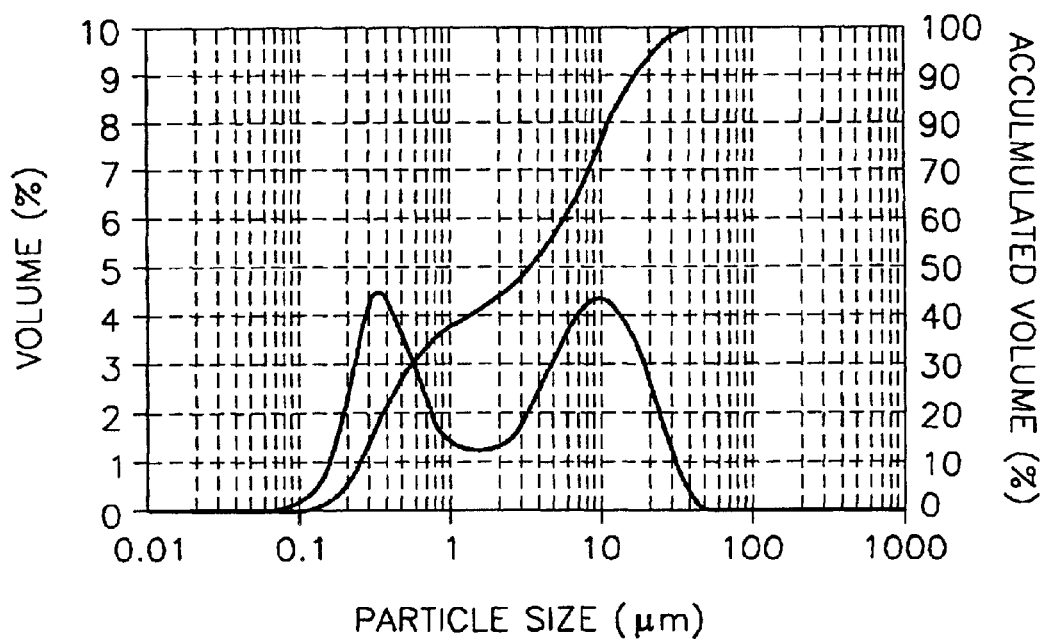

FIG. 2A shows the distribution characteristic of particle sizes before and FIG. 2B shows the distribution characteristic of particle sizes after pulverization.

Referring to FIGS. 2A and 2B, before pulverization, the particle size [D10], which is 10% of accumulated volume was approximately 0.4 μm and the particle size [D90], which is 90% of accumulated volume, was approximately 66 μm, respectively. After pulverization, the particle sizes [D10], [D50] and [D90] were approximately 0.3 μm, 3.5 μm and 16.6 μm, respectively. Approximately 50% of the organopolysulfide was pulverized to have a particle size of approximately 0.3 μm after pulverization and the remaining organopolysulfide had the distribution of 10 μm particle size, which was the main particle size before pulverization, resulting in the distribution of two kinds of particle sizes.

SYNTHESIS EXAMPLE 6

Preparation of cyclic bis (2,5-bis-dithio-1,4-dimethoxybenzene) Represented by Formula 1

2.09 g of cyclic bis (2,5-bis-dithio-1,4-dimethoxybenzene) represented by formula 1, which is a red-orange organopolysulfide, was obtained in the same manner as in Synthesis Example 5, except that 4 equivalents, rather than 2 equivalents, of SMC were used. The melting point of the organopolysulfide was 198–200° C., and the organopolysulfide turned out to have the same structure as the organopolysulfide prepared by Synthesis Example 5.

In addition to the red-orange organopolysulfide, a light yellow solid was obtained. The melting point of the solid was 118° C., the elemental analysis result showed that the content of sulfur was 99.3%, and the solid turned out to be elemental sulfur (S8) generated during the reaction.

In the organopolysulfide represented by formula 1, prepared by Synthesis Examples 5 and 6, the elemental analysis showed that the ratio of carbon to hydrogen to sulfur was 36:3:49, the synthesis formula was $C_{16}H_{16}O_4S_8$ and the molecular weight was 528 g/mol.

SYNTHESIS EXAMPLE 7

Preparation of Organopolysulfide Represented by Formula 5

(1) Molar ratio of 4,4'-ethylidenebisphenol to SMC=1:4

4,4'-Ethylidenebisphenol (10 mmol, 2.14 g) was dissolved in 40 ml of methylene chloride (MC) and cooled in an ice water bath, and then 4 equivalents of SMC (40 mmol, 3.2 ml) were added thereto over a 1 minute period. In order to remove toxic gases produced during the reaction, such as $Cl_2$ or HCl, a NaOH trap was installed at the entrance of a reaction flask, thereby removing toxic gases.

While being stirred initially, the reaction mixture turned red, but did not become cloudy, unlike bisphenol A. However, another hour of stirring, with the temperature of the ice water bath elevated to room temperature, resulted in a red precipitation from the reaction mixture. After the lapse of 7 days, a purple-red solid was produced.

The solid was filtered and washed with methylene chloride, and then the filtered solid was vacuum-dried at 80° C. to obtain a purple solid. The melting point of the purple solid was measured. Also, the content of sulfur contained in the purple solid was measured by elemental analysis.

The result of the analysis evidenced that the purple solid turned slightly in color at a temperature of around 240° C. and remained purple without being dissolved at 260° C. Also, the elemental analysis result showed that the ratio of carbon to hydrogen to oxygen to sulfur was 41.8:2.49:5.76:47.3. The result of the analysis ascertained that the obtained product was $(C_{14}H_{10}O_2S_8)_n$ bistetrasulfide series (n=1 or 2).

(2) Molar ratio of 4,4'-ethylidenebisphenol to SMC=1:8

4,4'-Ethylidenebisphenol (10 mmol, 2.14 g) was dissolved in 40 ml of MC and cooled in an ice water bath, and then 8 equivalents of SMC (80 mmol, 6.4 ml,) were added thereto over a 1 minute period. In order to remove toxic gases produced during the reaction, such as $Cl_2$ or HCl, a NaOH trap was installed at the entrance of a reaction flask, thereby removing rapidly produced toxic gases.

While being stirred initially, the reaction mixture turned red, but did not become cloudy, unlike bisphenol A. Even another hour of stirring, with the temperature of the ice water bath elevated to room temperature, did not result in a red precipitation from the reaction mixture. That is, the precipitate was produced later than the case where the molar ratio of 4,4'-ethylidenebisphenol to SMC was 1:4. After a lapse of 7 days, the reaction was terminated to obtain a purple-red solid.

The solid was filtered and washed with methylene chloride, and then the filtered solid was vacuum-dried at 80° C. to obtain a purple solid. The melting point of the purple solid so obtained was measured.

The result of the analysis evidenced that the purple solid turned slightly in color at a temperature of around 240° C., similarly to case (1), and remained brownish purple without being dissolved at 260° C. Also, the content of sulfur contained in the purple solid was measured by elemental analysis. The result of the elemental analysis showed that the ratio of carbon to hydrogen to oxygen to sulfur was 38.36:2.17:5.51:51.44. The result of the analysis ascertained that the product so obtained was $(C_{14}H_{10}O_2S_8)_n$ bistetrasulfide series (n=1 or 2), which is the same as in case (1), in consideration of experimental errors of elemental analysis.

From the above result, it was confirmed that the melting point of the organopolysulfide represented by formula 5 was 260° C. or higher. Also, the estimated theoretical capacity of the organopolysulfide represented by formula 5 was approximately 690 mAh/g in the case where only sulfur participates in capacity, and was 805 mAh/g in the case where an alcohol group accepts lithium.

SYNTHESIS EXAMPLE 8

Preparation of Organopolysulfide Represented by Formula 6

(1) Molar ratio of bisphenol A to SMC=1:4

Bisphenol A (10 mmol, 2.28 g) was dissolved in 40 ml of MC and 4 equivalents of SMC (40 mmol, 3.2 ml) were added thereto in an ice water bath over a 1 minute period. After the reaction mixture was stirred for 1 minute, a white solid was produced, and the mixture turned cloudy. Subsequently, the temperature of the reaction mixture was gradually elevated to room temperature, and the mixture was reacted for 7 days while stirring.

After a lapse of 7 days, a dark yellow solid was produced in the reaction mixture. The solid was filtered and washed with methanol, and then the filtered solid was vacuum-dried at 80° C. The melting point of the dark yellow solid so obtained was measured.

The result of the analysis evidenced that the solid slightly turned light brown at a temperature of around 220° C. and turned brown without being dissolved at 260° C. Also, the content of sulfur contained in the compound was measured by elemental analysis. The result of the elemental analysis showed that the ratio of carbon to hydrogen to oxygen to sulfur was 42.09:2.91:5.83:47.30.

(2) Molar ratio of bisphenol A to SMC=1:8

A dark yellow solid was obtained in the same manner as in case (1), except that 8 equivalents (80 mmol, 6.4 ml), rather than 4 equivalents, of SMC were used.

The result of the analysis evidenced that the dark yellow solid turned light yellow at a temperature of around 220° C., and turned brown without being dissolved at 260° C. Also, the solid was subjected to elemental analysis. The result of the elemental analysis showed that the ratio of carbon to hydrogen to oxygen to sulfur was 39.87:2.75:5.90:55.77. The result of the analysis ascertained that the obtained final product was $(Cl_5H_{12}O_2S_8)_n$ bistetrasulfide series (n=1 or 2), in consideration of experimental errors of elemental analysis.

From the above result, it was confirmed that the estimated theoretical capacity of the organopolysulfide represented by formula 6 was approximately 670 mAh/g in the case where only sulfur participates in capacity, and was 780 mAh/g in the case where an alcohol group accepts lithium.

SYNTHESIS EXAMPLE 9

Preparation of Organopolysulfide Represented by Formula 7

Hexabromobenzene ($C_6Br_6$) (4 mmol, 2.206 g) and 6.4 g of sulfur atoms were reacted in a 500 ml titanium hyperbaric reactor vessel in the presence of 240 ml of ammonia at 100° C. at 400 rpm for 24 hours.

After the 24-hour reaction, the temperature of the reaction mixture was adjusted to 80° C. An ammonia containing solution in the reaction mixture was transferred to a 1 liter round bottom flask including 500 ml of methylene chloride by jet spraying via a tube installed at the entrance of the hyperbaric reactor vessel.

Subsequently, ammonia was completely evaporated from the methylene chloride solution, and the solution was then filtered using a cannula equipped with a paper filter. The solid thus filtered was dried, and then subjected to thermal gravimetric analysis (TGA).

As a result, the solid residue was 99.00% at 136° C., 98.00% at 156.43° C., 95.00% at 183° C., and 25.76% at 300° C., respectively.

The red solid remaining after filtering using the cannula was washed with 500 ml methanol and 250 ml acetone to thus remove a trivial amount of unreacted sulfur and byproducts of ammonia. The reddish brown powder thus obtained was dried in a vacuum oven at 60° C. for 5 hours, thereby obtaining 1.07 g of organopolysulfide, which was subjected to elemental analysis.

The elemental analysis showed that the ratio of nitrogen to carbon to hydrogen to sulfur was 0.68:11.56:0.32:90.00 by percent, that is to say, the final product contains small amounts of nitrogen and hydrogen components. However, since the weight ratio of carbon to sulfur is 11.56:90, the number of sulfur atoms corresponding to 6 carbon atoms is 18.

Figure 4A:
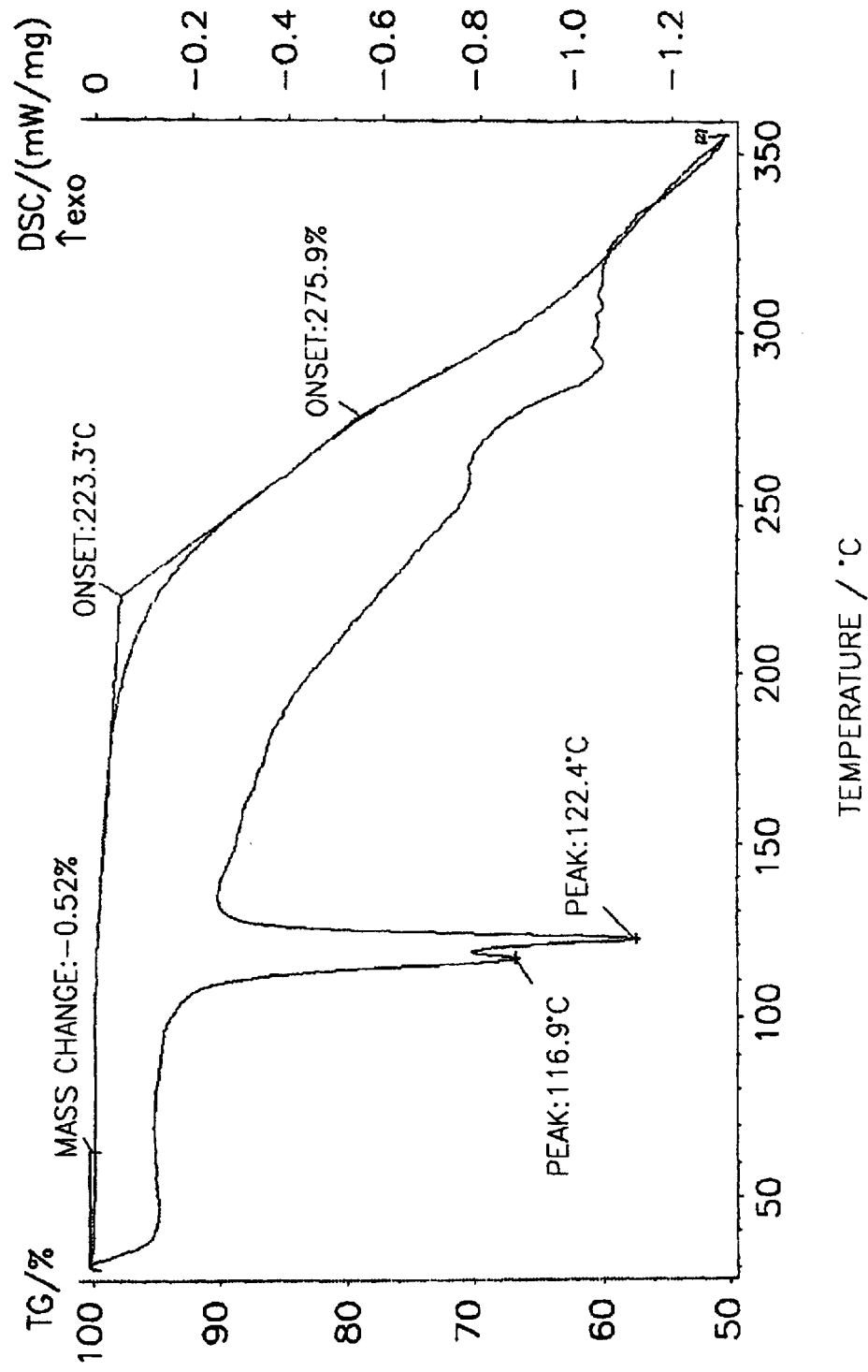
FIG. 4A illustrates the result of a thermal gravimetric analysis (TGA) of the organopolysulfide prepared by Example 9.

The estimated theoretical capacity of the organopolysulfide represented by formula 7 was approximately 1250 mAh/g. The result of the TGA performed on the prepared organopolysulfide is shown in FIG. 4A. Referring to FIG. 4A, the proportion of the volatile components of the prepared organopolysulfide is approximately 0.52%, the melting points (Tm) are 116.9° C. and 122.4° C., and the decomposition temperatures (Td) are 223.3° C. and 275.9° C.

Figure 4B:
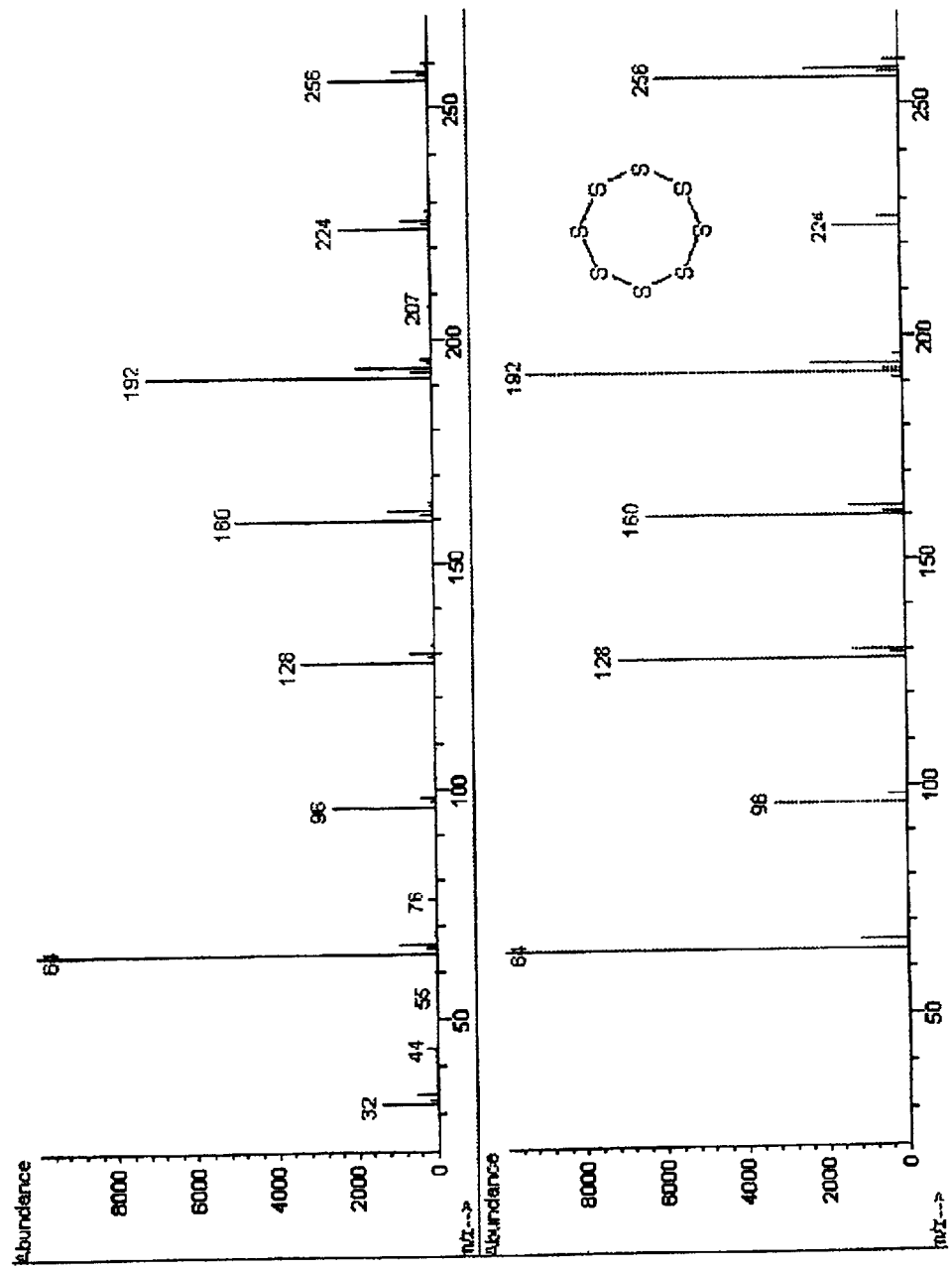
FIG. 4B illustrates the result of a mass analysis of the organopolysulfide prepared by Example 9.
Figure 5:
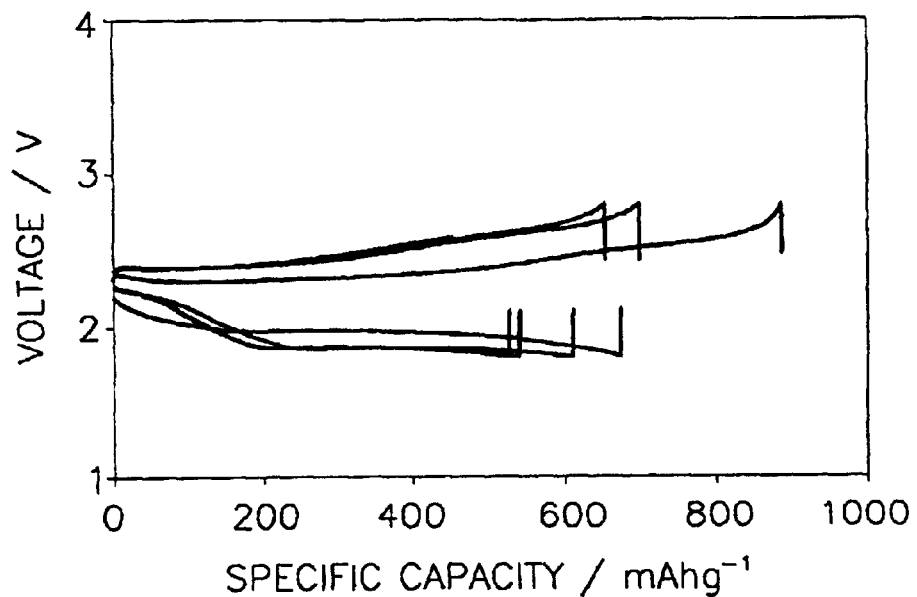
FIG. 5 illustrates charging/discharging characteristics of the organopolysulfide prepared by Example 9.

FIG. 4B shows the result of the GC-mass analysis of the organopolysulfide prepared by Synthesis Example 9. Referring to FIG. 4B, the organopolysulfide has an octagonal ring structure A battery was fabricated using the organopolysulfide, and charging/discharging tests were carried out. FIG. 5 shows the result of the charging/discharging tests under the following conditions: an initial charge current rate of 0.25C, and a discharge current rate of 0.5C.

Referring to FIG. 5, the charge capacity was approximately 675 mAh/g and a 0.5C discharge capacity was 610 mAh/g.

EXAMPLE 1

Fabrication of Lithium/Sulfur Polymer Electrolyte Battery 52.09 g of the organopolysulfide obtained by Synthesis 5, 14.81 g of Super P. black, 29.11 g of polyethylene oxide 900,000 having a weight average molecular weight of 900,000, 3.98 g of $LiOSO_2CF_3$(LiOTf), which is a lithium salt, and 734 ml of acetonitrile were mixed to prepare a composition for a cathode active material.

The cathode active material composition was coated on a nickel thin film having a thickness of 10 μm and dried in a dry box under room temperature and room pressure.

Thereafter, the dried electrode was vacuum-pressed at room temperature to fabricate a cathode.

Separately from the above, lithium metal was roll-pressed thinly on a copper thin film to fabricate an anode.

A porous polypropylene film (product name: Cellgard 2500) was disposed between the cathode and the anode and then a lithium/sulfur polymer electrolyte battery was fabricated using 1 M $LiClO_4$ dissolved in a solvent mixture of EC and DMC in the ratio by volume of 1:1 as an electrolytic solution.

EXAMPLE 2

A lithium/sulfur polymer electrolyte battery was fabricated in the same manner as in Example 1, except that the composition for forming a cathode active material was prepared as follows.

83.84 g of the organopolysulfide obtained by Synthesis Example 5, 4.55 g of Super P. black, 10.10 g of polyethylene oxide 900,000 having a weight average molecular weight of 900,000, 2.02 g of LiOTf, which is a lithium salt, and 253 ml of acetonitrile were mixed to prepare the cathode active material composition.

EXAMPLE 3

A lithium/sulfur polymer electrolyte battery was fabricated in the same manner as in Example 1, except that the composition for forming a cathode active material was prepared as follows.

81.82 g of the organopolysulfide obtained by Synthesis Example 5, 5.05 g of Super P. black, 10.15 g of polyethylene oxide 900,000 having a weight average molecular weight of 900,000, 3.55 g of LiOTf, which is a lithium salt, and 253 ml of acetonitrile were mixed to prepare the cathode active material composition.

EXAMPLE 4

A lithium/sulfur polymer electrolyte battery was fabricated in the same manner as in Example 1, except that composition for forming a cathode active material was prepared as follows.

62.81 g of the organopolysulfide obtained by Synthesis Example 5, 5.03 g of Super P. black, 9.60 g of polyethylene oxide 900,000 having a weight average molecular weight of 900,000, 2.02 g of LiOTf, which is a lithium salt, and 431 ml of acetonitrile were mixed to prepare the cathode active material composition.

EXAMPLE 5

A lithium/sulfur polymer electrolyte battery was fabricated in the same manner as in Example 1, except that the composition for forming a cathode active material was prepared as follows.

62.56 g of the organopolysulfide obtained by Synthesis Example 5, 4.10 g of Super P. black, 9.60 g of polyethylene oxide 900,000 having a weight average molecular weight of 900,000, 3.54 g of LiOTf, which is a lithium salt, and 431 ml of acetonitrile were mixed to prepare the cathode active material composition.

EXAMPLE 6

A lithium/sulfur polymer electrolyte battery was fabricated in the same manner as in Example 1, except that the composition for forming a cathode active material was prepared as follows.

73.23 g of the organopolysulfide obtained by Synthesis Example 5, 14.65 g of Super P. black, 30.15 g of polyethylene oxide 900,000 having a weight average molecular weight of 900,000, 2.01 g of LiOTf, which is a lithium salt, and 557 ml of acetonitrile were mixed to prepare the cathode active material composition.

EXAMPLE 7

A lithium/sulfur polymer electrolyte battery was fabricated in the same manner as in Example 1, except that the composition for forming a cathode active material was prepared as follows.

72.08 g of the organopolysulfide obtained by Synthesis Example 5, 14.21 g of Super P. black, 29.23 g of polyethylene oxide 900,000 having a weight average molecular weight of 900,000, 4.10 g of LiOTf, which is a lithium salt, and 557 ml of acetonitrile were mixed to prepare the cathode active material composition.

EXAMPLE 8

A lithium/sulfur polymer electrolyte battery was fabricated in the same manner as in Example 1, except that the composition for forming a cathode active material was prepared as follows.

53.30 g of the organopolysulfide obtained by Synthesis Example 5, 15.23 g of Super P. black, 29.44 g of polyethylene oxide 900,000 having a weight average molecular weight of 900,000, 2.03 g of LiOTf, which is a lithium salt, and 734 ml of acetonitrile were mixed to prepare the cathode active material composition.

Figure 6A:
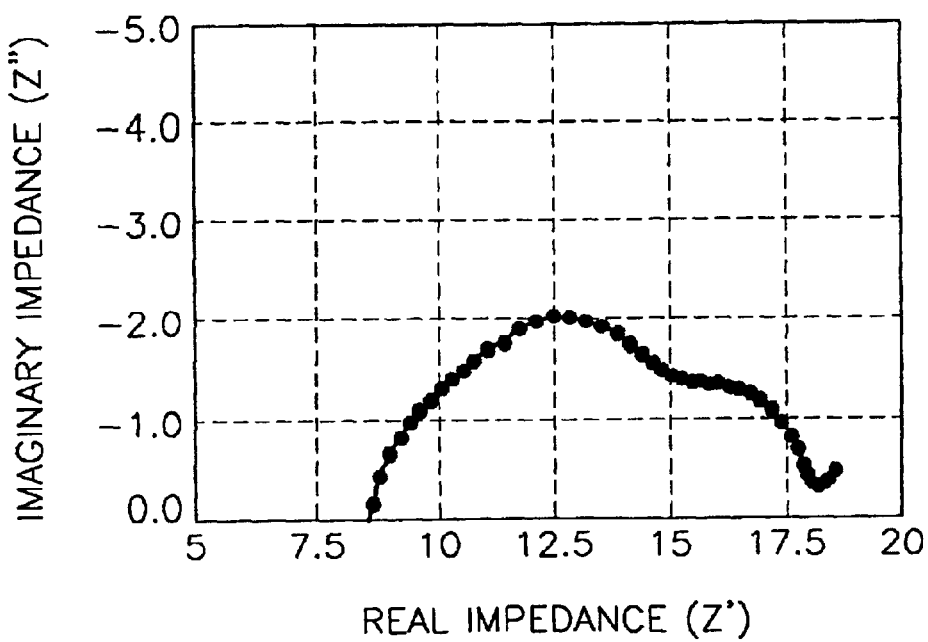
FIG. 6A illustrates the result of an impedance measurement of a lithium/sulfur polymer electrolyte battery prepared by Example 1, and FIG. 6B collectively illustrates the results of impedance measurements of lithium/sulfur polymer electrolyte batteries prepared by Examples 1 through 8.
Figure 6B:
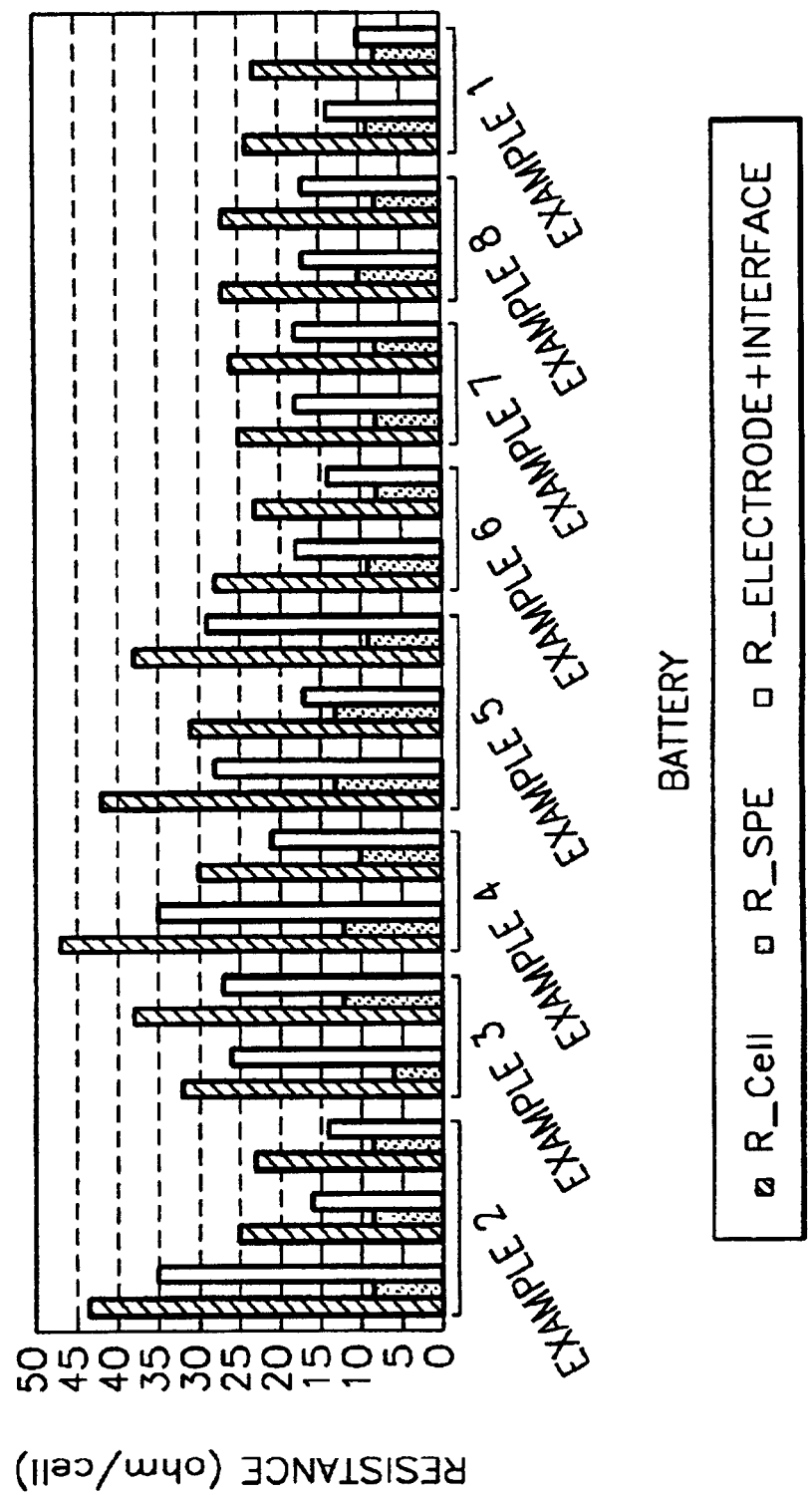

The impedance characteristics of the lithium/sulfur polymer electrolyte batteries prepared by the above-described procedure were examined, and the results thereof are shown in FIGS. 6A and 6B. Here, the impedance characteristic of the prepared batteries were measured at 80° C. and 50 mV of potential altitude using a Jahner IM6 impedance analyzer in the frequency range of 700 mHz to 500 kHz.

FIG. 6A shows the result of the measurement of impedance of a lithium/sulfur polymer electrolyte battery prepared by Example 1. Referring thereto, when the resistance of a lead wire is negligible, the resistance R_SPE of a solid polymer electrolyte (SPE) was approximately 10 Ω.

FIG. 6B collectively shows the results of the measurement of the impedance characteristics of the batteries prepared by Examples 1 through 8. Referring thereto, when the content of Super P. Black was 4 to 5 parts by weight based on 100 parts by weight of the solid matter of the cathode active material composition as in Examples 2 through 5, the interface resistance between an electrode and a solid polymer electrolyte was smaller than when the content of Super P. Black was 14 to 15 parts by weight as in Examples 1 and 6 through 8. Also, if the content of polyethylene oxide which is a binder, is 10 parts by weight as in Examples 2 and 3, and is 29 parts by weight as in Example 1, the sums of the electrode resistance and interface resistance between the electrode and the solid polymer electrolyte was 17.9 Ω and 11.7 Ω, respectively, that is, the resistance in the case of 29 parts by weight of polyethylene oxide (Example 1) was relatively smaller.

Also, when the contents of the lithium salt LiOTf were approximately 2 parts by weight and 4 parts by weight based on 100 parts by weight of the solid matter of the cathode active material composition, respectively, the resistance values were 16.6 Ω and 11.7 Ω, respectively. That is, the higher the content of lithium salt, the lower the resistance value.

As described above, as the contents of the conductive agent, polyethylene oxide and lithium salt increased, the impedance characteristics of a battery become poorer.

Figure 7A:
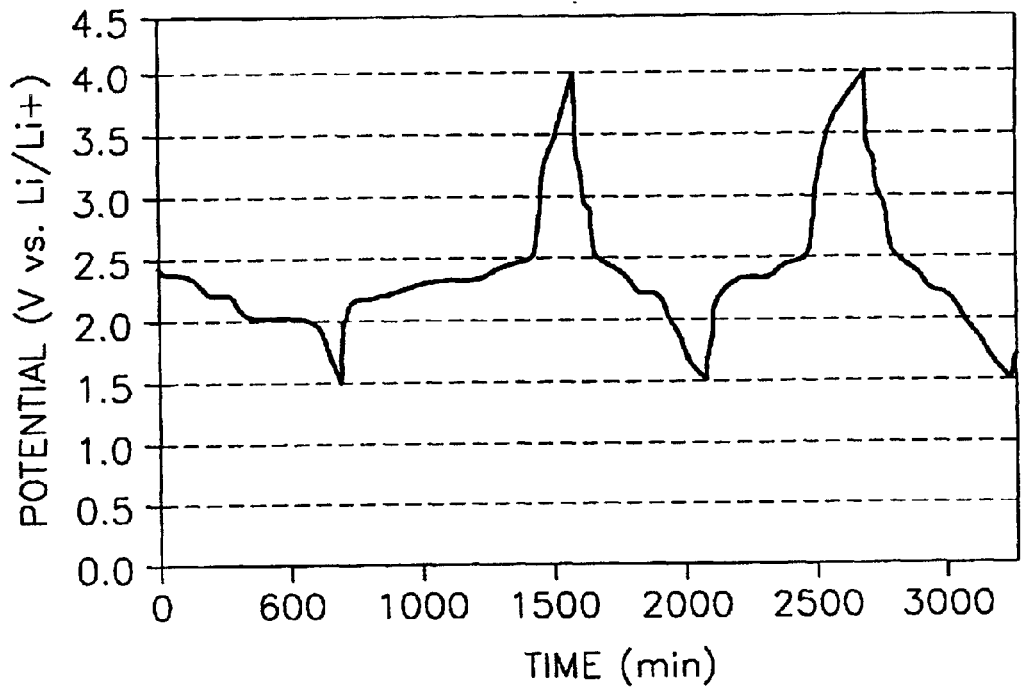
FIG. 7A is a diagram illustrating a change in the potential depending on charging/discharging in a lithium/sulfur polymer electrolyte battery prepared by Example 1.
Figure 7B:
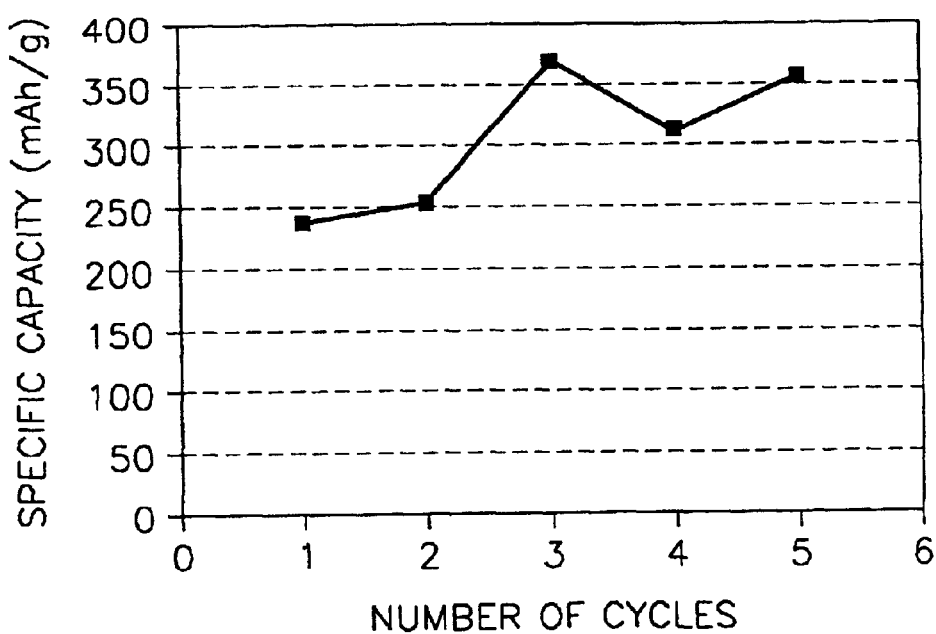
FIG. 7B is a diagram illustrating a change in the specific discharge capacity depending on charging/discharging in a lithium/sulfur polymer electrolyte battery prepared by Example 1.

Next, a charging/discharging test was carried out on the lithium/sulfur polymer electrolyte battery prepared by Example 1. The charging/discharging test was carried out using a Toscat 3000 charging/discharging tester under a constant-current condition. The current was C/12 rate with respect to a theoretical capacity of each battery, and the upper-limit charging voltage and lower-limit discharging voltage were controlled to be 4.0 V and 1.5 V, respectively. Also, a 30 minute pause was provided between each charging and discharging so that the battery reached a state of thermodynamic equilibrium. The constant-current charging/discharging test results are shown in FIGS. 7A and 7B. FIG. 7A shows a change in the potential according to charging and discharging, and FIG. 7B shows a change in the specific discharge capacity according to charging and discharging.

Referring to FIG. 7A, the lithium/sulfur polymer battery showed a relatively planar potential region ranging around 2.4 V, 2.2 V and 2.0 V during discharging. In particular, the main potential range of the discharging reaction occurred around 2.0 V. Also, the battery had an average discharge voltage of 2.1 V. During charging, the planar potential region ranged from 2.2 V to 2.5 V, and the capacity between 2.5 V and 4.0 V was small. Thus, the main potential range of the discharging reaction in the battery was 2.0 V to 2.5 V.

The specific discharge capacity shown in FIG. 7B is the capacity of a battery per unit weight of a cathode material. The primary specific discharge capacity was approximately 240 mAh/g, which is 75% greater than that of the specific discharge capacity, that is, 137 mAh/g, of lithium cobalt oxide ($LiCoO_2$) of the lithium ion battery. If the number of charging/discharging cycles was increased to 5 times, the specific capacity was approximately 350 mAh/g, which is 255% greater than lithium cobalt oxide.

Also, with respect to the batteries prepared by Examples 1 through 8, a constant-current charging/discharging test was carried out using C/12 rate current. Here, the theoretical capacities of the batteries prepared by the Examples were calculated from the theoretical specific capacity of the cathode active material Char represented by formula 1, that is, 609 mAh/g (based on the molecular weight of the cathode active material represented by formula 1, that is, 528 g) and the weight of the cathode active material contained in the cathode.

Figure 8A:
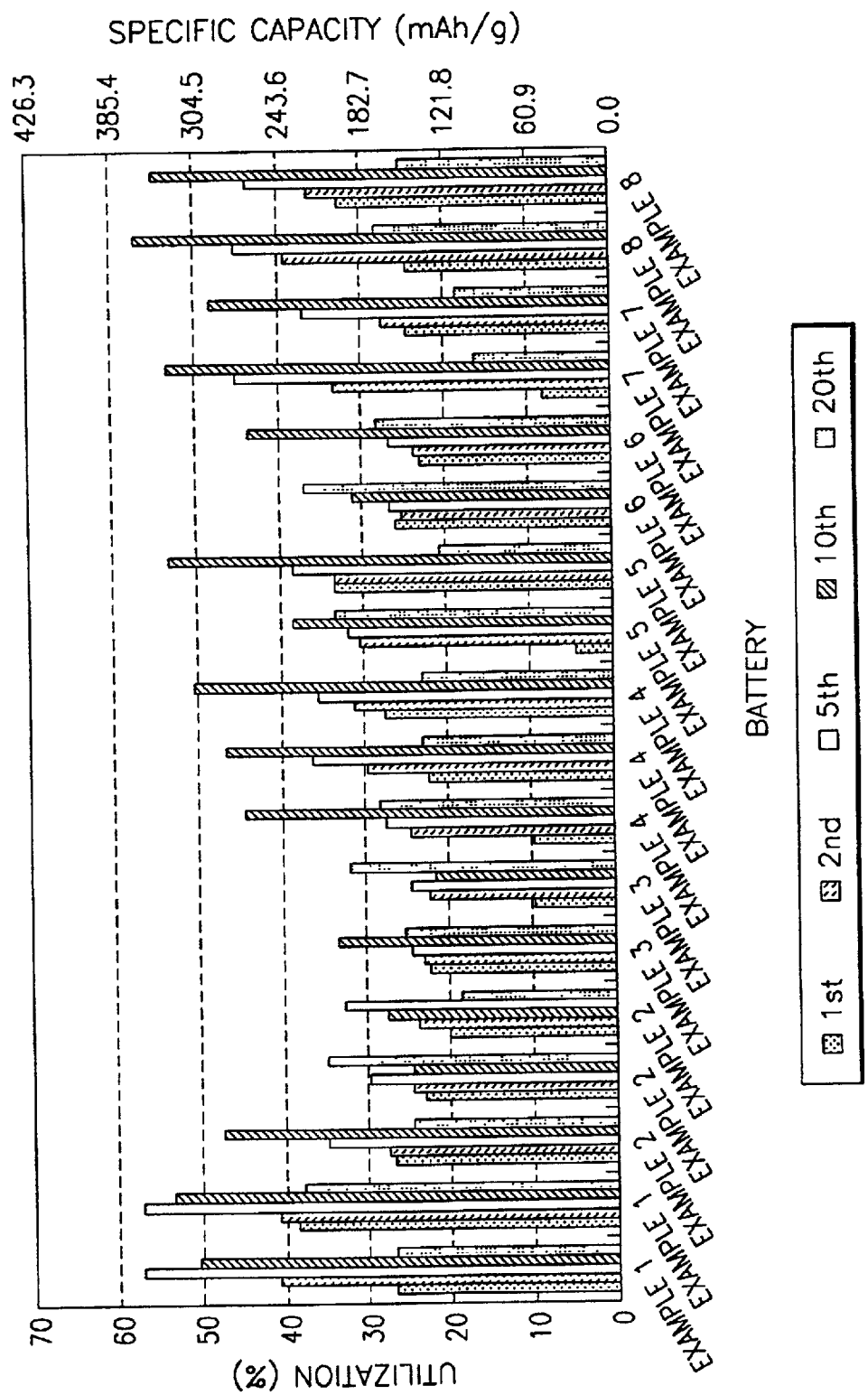
FIGS. 8A and 8B collectively illustrate the specific capacity, utilization efficiency, impedance, charging/discharging efficiency and initial charging recovery rate of batteries prepared according to the invention.
Figure 8B:
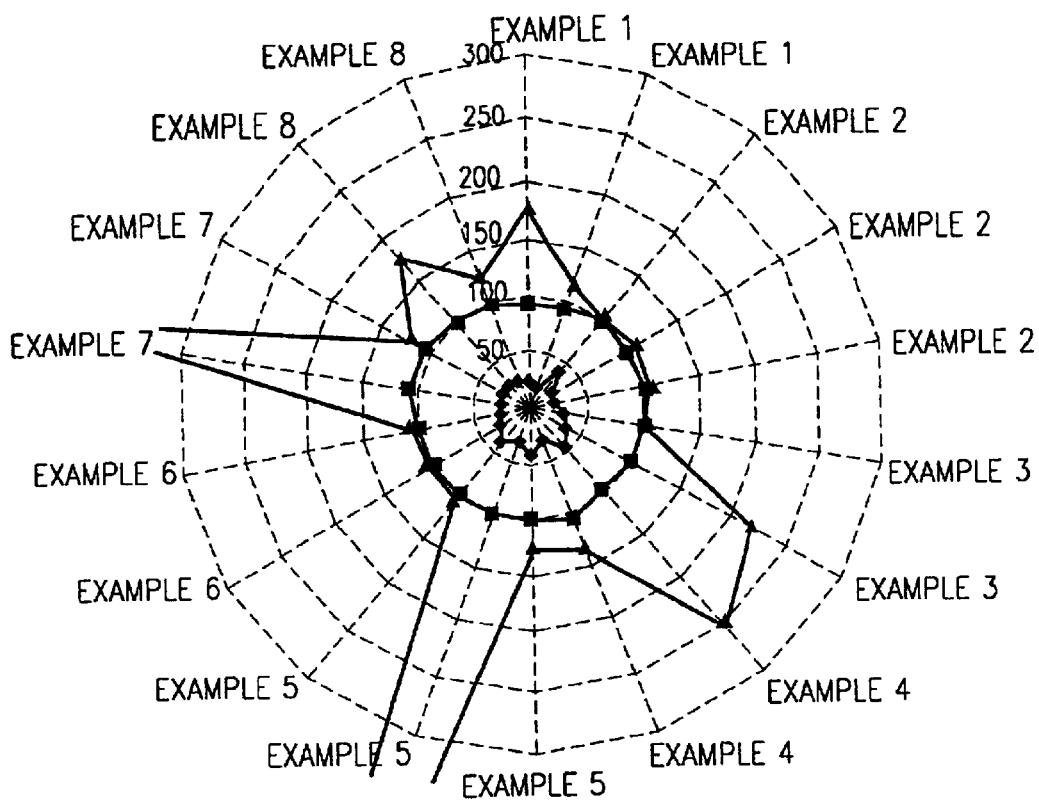
Figure 8B:
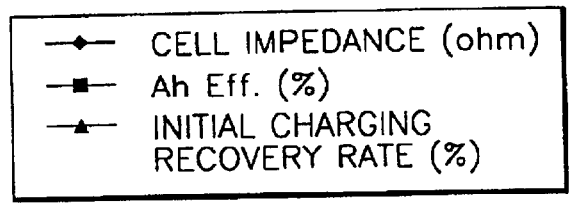

With respect to the batteries prepared by Examples 1 through 8, the theoretical specific capacity and actually measured specific capacity, impedance characteristics and impedance values, utilization efficiency, initial charging recovery rate (Qc1/Qd1) and primary charging/discharging efficiency (Qd2/Qc1), obtained from the charging/discharging test results, were measured, and the results thereof are shown in FIGS. 8A–B. Here, the utilization efficiency is the ratio of the specific capacity obtained from the actual reaction to the theoretical specific capacity of organic sulfur material capable of reacting with lithium, and the maximum value thereof is 100%. The initial charging recovery rate is the ratio of the initial charged amount to the initial discharged amount, and is related to the stability of a battery. As the value of the initial charging recovery rate approaches 100%, the initial charging recovery rate improves. The primary charging/discharging efficiency is the ratio of the subsequently discharged amount to the primary charged amount. The closer to 100% the primary charging/discharging efficiency is, the better the battery is.

Referring to FIGS. 8A and 8B, the first utilization efficiency of a low impedance battery was stabilized at a high level. The first utilization efficiency of the battery prepared by Example 1 was approximately 39%, and that of the battery prepared by Example 8 was approximately 33%. The second utilization efficiencies of the batteries were similar to the first utilization efficiencies. The second utilization efficiencies of the batteries prepared by Examples 1 and 8 were relatively high, that is, approximately 40%. Also, the fifth utilization efficiency relatively increased compared to the primary charging/discharging. During the initial charging/discharging test, even the batteries having the same composition showed rather different the specific capacities. However, as the number of cycles increased, the specific capacities became similar.

The primary specific discharge capacity of the battery prepared by Example 1 was 240 mAh/g, the initial charging recovery rate was 114.5%, and the primary charging/discharging efficiency was 92.5%. The measured values for batteries prepared by the respective Examples are summarized below in Table 1.

TABLE 1

|  | Primary specific discharge capacity (mAh/g) | Initial charging recovery rate (Qc1/Qd1, %) | Primary charging/discharging efficiency (Qd2/Qc1, %) |
| --- | --- | --- | --- |
| Example 1 | 240 | 114.5 | 92.5 |
| Example 2 | 168 | 100.3 | 102.5 |
| Example 3 | 141 | 99.8 | 103.3 |
| Example 4 | 142 | 127.7 | 102.0 |
| Example 5 | 171 | 120.9 | 93.6 |
| Example 6 | 163 | 101.0 | 95.9 |
| Example 7 | 148 | 114.7 | 101.9 |
| Example 8 | 202 | 118.4 | 94.9 |

As described above, cyclic bis (2,5-bis-dithio-1,4-dimethoxybenzene) represented by formula 1 is easy to process with respect to particle size, and has excellent electrochemical utilization efficiency and a high capacity, that is, 610 mAh/g in theoretical capacity. Also, cyclic bis (2,5-bis-dithio-1,4-dimethoxybenzene) represented by formula 1 has high stability against air, moisture and heat, and does not dissolve well in an electrolytic solution. Further, the raw materials of cyclic bis (2,5-bis-dithio-1,4-dimethoxybenzene) represented by formula 1 are highly competitive in price and are easily separated and refined during synthesis. If cyclic bis (2,5-bis-dithio-1,4-dimethoxybenzene) represented by formula 1 is employed as a cathode active material, a 2V-class pollution-free high-energy lithium secondary battery having excellent capacity and cycle characteristics can be developed. The lithium secondary battery is particularly suitable for next-generation up-to-date electronic devices driven at 1.5–1.8 V and can be widely and promisingly applied small electronic devices for military, non-military and aerospace uses. Also, due to the large-capacity and high-voltage tendency of the lithium secondary battery according to the present invention, it can also be used with high-level wirelessly powered devices such as electric motors, battery electricity, submarines or electric trains.

While the invention has been described in detail and with reference to specific examples thereof, it will be apparent to one skilled in the art that various changes and modifications can be made therein without departing from the spirit and scope thereof. Therefore, it is intended that a true scope and spirit of the invention be defined solely by the appended claims.

What is claimed is:

1. A cathode active material comprising cyclic bis (2,5-bis-dithio-1,4-dimethoxybenzene) represented by formula 1 a conductive agent and a binder:

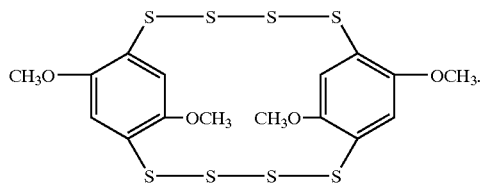

1

2. A lithium battery comprising:

a cathode having a cathode active material layer comprising cyclic bis (2,5-bis-dithio-1,4-dimethoxybenzene) represented by formula 1, a conductive agent and a binder;

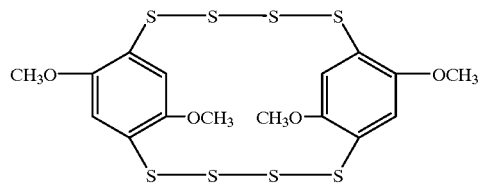

1 an anode having an anode layer comprising lithium metal or a lithium alloy; and a separator interposed between the cathode and the anode.

3. The lithium battery according to claim 2, wherein the binder comprises at least one selected from the group consisting of polyethylene oxide (PEO), polyacrylonitrile (PAN), polymethyl methacrylate (PMMA), polyvinylidene fluoride (PVDF), acrylonitrile-methyl methacrylate-styrene terpolymer (AMS), vinylidene fluoride-hexafluoropropylene (VDF-HFP) copolymer, polyvinyl chloride (PVD) and cellulose.

4. The lithium battery according to claim 2, wherein the conductive agent comprises at least one selected from the group consisting of carbon black, acetylene black and vapor growth carbon fiber (VGCF).

5. The lithium battery according to claim 2, wherein the separator comprises at least one selected from the group consisting of polyethylene oxide (PEO), polyacrylonitrile (PAN), polymethyl methacrylate (PMMA), polyvinylidene fluoride (PVDF), acrylonitrile-methylmethacrylate-styrene terpolymer (AMS), vinylidenefluoride-hexafluoropropylene (PVDF-HFP) copolymer, polyvinyl chloride (PVD) and cellulose.

* * * * *